United States Patent
Miller et al.

(10) Patent No.: US 11,696,807 B2
(45) Date of Patent: Jul. 11, 2023

(54) DROP DETECTION OF UNGROUNDED MASTER CONTROLLER FOR A SURGICAL ROBOT

(71) Applicant: Verb Surgical Inc., Santa Clara, CA (US)

(72) Inventors: Denise Ann Miller, Scotts Valley, CA (US); Joan Savaii, Palo Alto, CA (US); Randall Blake Hellman, San Francisco, CA (US)

(73) Assignee: Verb Surgical Inc., Santa Clara, CA (US)

( * ) Notice: Subject to any disclaimer, the term of this patent is extended or adjusted under 35 U.S.C. 154(b) by 671 days.

(21) Appl. No.: 16/821,798

(22) Filed: Mar. 17, 2020

(65) Prior Publication Data
US 2021/0290328 A1 Sep. 23, 2021

(51) Int. Cl.
*B25J 13/00* (2006.01)
*B25J 13/06* (2006.01)
(Continued)

(52) U.S. Cl.
CPC .............. *A61B 34/70* (2016.02); *A61B 34/25* (2016.02); *A61B 34/37* (2016.02); *A61B 90/06* (2016.02);
(Continued)

(58) Field of Classification Search
CPC .. A61B 34/37; A61B 2090/065; B25J 13/006; B25J 13/02
See application file for complete search history.

(56) References Cited

U.S. PATENT DOCUMENTS

| | | | |
|---|---|---|---|
| 2014/0148820 A1* | 5/2014 | Ogawa | A61B 34/77 606/130 |
| 2014/0160015 A1* | 6/2014 | Ogawa | A61B 34/37 345/156 |

(Continued)

FOREIGN PATENT DOCUMENTS

WO 2016/171757 A1 10/2016

OTHER PUBLICATIONS

International Search Report and Written Opinion of the PCT Patent Office dated Nov. 12, 2020 for related PCT Patent Application No. PCT/US2020/030871.
(Continued)

*Primary Examiner* — Kira Nguyen
(74) *Attorney, Agent, or Firm* — Aikin & Gallant, LLP

(57) ABSTRACT

Disclosed herein are methods to detect a free-falling or other non-surgical motions of the user interface device (UID) of a surgical robotic system so that the surgical robotic system may pause the robotic arm controlled by the UID to prevent the robotic arm from mimicking the unintentional movement of the UID. Contact sensors embedded in the UID may be used to detect conditions indicating that a user does not possess full control of the UID. After determining that the user does not have full control of the UID, the UID may detect if the UID is experiencing non-surgical motions using motion sensors such as inertial sensors. By conditioning analysis of the data from the motion sensors by the initial determination that the UID is not being held based on the contact sensors, the method increases the robustness of the detection of non-surgical motions and reduces the probability of false positives.

20 Claims, 7 Drawing Sheets

(51) Int. Cl.
  *A61B 34/37*   (2016.01)
  *A61B 34/00*   (2016.01)
  *A61B 90/00*   (2016.01)
  *B25J 13/02*   (2006.01)

(52) U.S. Cl.
  CPC ............ *B25J 13/006* (2013.01); *B25J 13/02* (2013.01); *A61B 2090/065* (2016.02); *A61B 2562/0219* (2013.01)

(56) References Cited

U.S. PATENT DOCUMENTS

| | | | |
|---|---|---|---|
| 2014/0277747 A1* | 9/2014 | Walker | A61B 34/30 |
| | | | 700/275 |
| 2018/0078319 A1* | 3/2018 | Nobles | A47B 21/03 |
| 2018/0161108 A1* | 6/2018 | Savall | G06F 3/033 |
| 2018/0168759 A1* | 6/2018 | Kilroy | B25J 13/086 |
| 2019/0380801 A1 | 12/2019 | Savall et al. | |
| 2019/0380802 A1 | 12/2019 | Savall et al. | |
| 2020/0046439 A1* | 2/2020 | Tekiela | A61B 34/20 |

OTHER PUBLICATIONS

International Preliminary Reporton Patentability for International Application No. PCT/US2020/030871 dated Sep. 29, 2022, 10 page.

\* cited by examiner

DROP DETECTION OF UNGROUNDED MASTER CONTROLLER FOR A SURGICAL ROBOT

TECHNICAL FIELD

The subject technology generally relates to robotics and surgical systems, and more specifically to user interface devices or controllers that allow users to manipulate surgical robotic arms or surgical tools mounted on the surgical robotic arms to perform minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., an end effector, endoscope, etc.) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end a device such as a surgical end effector, an imaging device, a cannula for providing access to the patient's body cavity and organs, etc. In robotic MIS systems, it is important to establish and maintain high positional accuracy for the surgical instrument supported by the robotic arm.

To enable a surgeon to command highly dexterous, precise movement of surgical actuators and robotic surgical tools, robotically-assisted surgical systems may include a user interface device (UID) or a controller that the surgeon may hold in her hand. The surgeon may manipulate the UID to control the robotic arm through a full range of spatial motion and orientation so that the surgical tool may mimic the movement of the UID when positioning the surgical tool. The surgeon may also manipulate the UID to control the operation of the surgical tools, such as grasping, cutting, suturing, etc. To prevent inadvertent movements and operations of the robotic arm and the attached surgical tool from harming the patients when the UID is dropped or inadvertently moved, a safety mechanism may be built in.

SUMMARY

A robotically-assisted surgical system, also referred to as a surgical robotic system, is a software-controlled, electromechanical system designed for surgeons to perform minimally-invasive surgeries. An ungrounded user interface device (UID) of the surgical robotic system allows a surgeon to perform highly dexterous, precise movement of a surgical actuator and robotic surgical tool. For example, the surgeon may manipulate the UID in her hand to control a robotic arm and the surgical tool attached to the robotic arm through six degrees of freedom, including physical displacement (e.g., translation in XYZ space or another suitable coordinate system), and orientation (e.g., roll, pitch, yaw). The UID may include a tracking sensor (e.g., a six-degree-of-freedom electromagnetic tracker) that generates a spatial state signal in response to movements of the UID. The spatial state signal may be used by a processor to control a spatial motion of an actuator of the robotic arm or the attached surgical tool to mimic the spatial motion of the UID in the hand of the surgeon. To prevent unintentional movements of the robotic arm and the surgical tool caused by unintentional movements of the UID from harming the patients, such as when the UID is dropped, the UID may have a built-in safety mechanism.

Disclosed herein are methods to detect a free-falling or other non-surgical motions of the UID so that the surgical robotic system may disengage or pause the robotic arm controlled by the UID to prevent the robotic arm from mimicking the unintentional movement of the UID. In one embodiment, a combination of sensors embedded in the UID may be used to detect conditions indicating that a user does not possess full control of the UID. For example, one or more proximity or contact sensors in the UID may detect that the surgeon's hand is not in close proximity or in contact with the UID for a minimum amount of time. Proximity or contact sensors may be capacitive, optical, thermal, etc., and may be placed at various locations on the UID to determine if the UID is being held or not. If the UID is being held, based on the locations of the sensors and the sensed signals, the UID may also determine if the UID is being held by fingers or is resting on the user's hand. If the UID is being held by fingers, such as in a grip, the tightness of the grip or the number of fingers used may also be determined. The method may use information on which part of the hand is contacting the UID, which part of the UID the user is contacting, the strength of the contact, etc., to determine if the user does not have full control of the UID for a threshold period of time. The threshold period of time may be a function of how and where the user is holding the UID.

After determining that the user does not have full control of the UID for the threshold period of time, the UID may detect if the UID is experiencing non-surgical motions using motion sensors such as inertial sensors. In one embodiment, the inertial sensors may detect velocity, acceleration, and jerk along the three-dimensional XYZ space to recognize non-surgical motions such as bobbling, throwing, swinging, freefalling, etc., of the UID. For example, an acceleration magnitude of 0 in the vertical direction may indicate a freefall drop. A high jerk may indicate bobbling or throwing. A high acceleration may indicate throwing or swinging. A high rotational acceleration or velocity may indicate slipping, rolling or throwing of the UID. By conditioning the sensed data from the motion sensors by the initial determination that the UID is not being held based on the proximity or contact sensors, the method increases the robustness of the detection of non-surgical motions and reduces the probability of false positives.

In one aspect, the UID may include a finger clutch that allows a user to pause the motion of the robotic arm and the corresponding surgical tool. For example, when a user touches the sensor area of the finger clutch with an index finger, the UID may generate a clutch signal to disengage the robotic arm and the surgical tool that is being manipulated by the UID. This may be useful when the user needs to reposition the UID within the virtual workspace to allow for additional movement in the direction of the workspace edge after the user has reached the edge of the virtual workspace. After disengaging the surgical tool from the movement of the UID using the finger clutch, the user may position the UID within the workspace, and then remove the finger from the finger clutch to re-engage the robotic arm and the surgical tool to the movement of the UID. In one embodiment, to provide a safeguard against the user not touching the finger clutch sensor with sufficient force when repositioning the UID within the workspace, the finger clutch sensor may determine if there is an anomaly in the user's control of the finger clutch. For example, the finger clutch sensor may detect that the user's finger is not fully touching the finger clutch sensor for a threshold period of time. Based on this determination, the UID may detect if the UID is experiencing non-surgical motions using the motion sensors. If the motion sensors detect that the UID is experiencing velocity, acceleration, or jerk that exceeds a maximum threshold or that lasts longer than a threshold period of time, the method may indicate non-surgical motions.

In one embodiment, a method for controlling a surgical robotic system is disclosed. The method includes sensing by the UID contact data from contact sensors. The contact data indicate contact by a user of surface areas of interest of the UID. The method also includes determining that the UID is not being held by the user based on the contact data and determining whether the length of time that the UID is not being held by the user is greater than a time threshold. The method further includes sensing by the UID motion data from one or more tracking sensors when the UID is determined as not being held by the user for greater than the time threshold. The method further includes determining a free-falling motion of the UID based on the motion data. The method further includes activating a safety mechanism to decouple the surgical robotic system from a movement of the UID when the free-falling motion of the UID is detected.

In one embodiment, an UID for controlling a surgical robotic system is disclosed. The UID includes contact sensors that generate contact data indicating contact by a user of surface areas of interest of the UID. The UID also includes tracking sensors that generate motion data of the UID. The UID includes a processor. The processor determines if the UID is not being held by the user for a duration greater than a time threshold based on the contact data. The processor also determines if there is a free-falling motion of the UID based on the motion data. Based on the determination that the UID is not being held by the user for longer than the time threshold and that the UID is experiencing a free-falling motion, the processor activates a safety mechanism to decouple the surgical robotic system from a movement of the UID.

BRIEF DESCRIPTION OF THE DRAWINGS

The accompanying drawings are provided together with the following description of various aspects and embodiments of the subject technology for a better comprehension of the invention. The drawings and the embodiments are illustrative of the invention, and are not intended to limit the scope of the invention. It is understood that a person of ordinary skill in the art may modify the drawings to generate drawings of other embodiments that would still fall within the scope of the invention.

DETAILED DESCRIPTION

Figure 1:
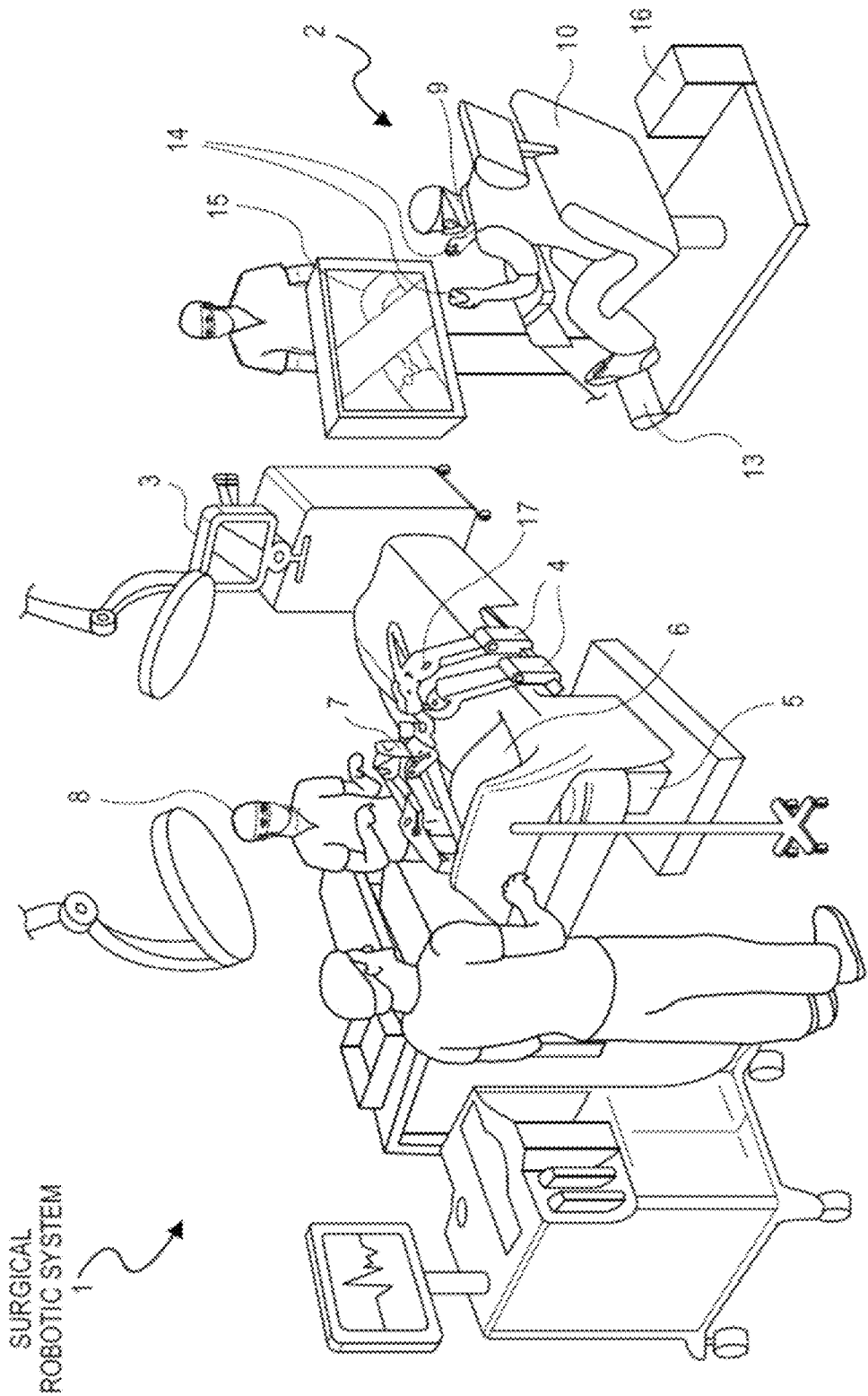
FIG. 1 is a pictorial view of an example surgical robotic system 1 in an operating arena, in accordance with aspects of the subject technology.

Examples of various aspects and variations of the subject technology are described herein and illustrated in the accompanying drawings. The following description is not intended to limit the invention to these embodiments, but rather to enable a person skilled in the art to make and use this invention.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of a UID to a specific configuration described in the various embodiments below.

Methods are disclosed herein for detecting a free-falling or other non-surgical motions of ungrounded UID of a surgical robotic system to prevent unintentional movements and operations of the engaged robotic arm and the surgical tool. A combination of proximity or contact sensors and motion or tracking sensors may be used to detect the non-surgical motions. The proximity or contact sensors may sense where, how, and whether the UID is being held by which part of a user's hand. The method may use sensed signals from, and location information of, the proximity or contact sensors to make a threshold determination that the user does not have full control of the UID for a threshold period of time or that the UID is engaged with the robotic arm and the surgical tool when it should not be. Based on this threshold determination, the method may analyze the sensed data from the motion or tracking sensors to determine if the UID is experiencing non-surgical motions involving high velocity, acceleration, or jerk. The method may disengage the robotic arm and the surgical tool from the movement of the UID if the detected non-surgical motion exceeds a threshold or lasts greater than a threshold duration. By combining the sensed data from the proximity or contact sensors and that from the motion or tracking sensors, such as by gating the analysis of the motion of the UID detected by the motion or tracking sensors based on how the UID is being held as detected by the proximity or contact sensors, the method increases the robustness of the detection of non-surgical motions and reduces the probability of false positives. The method may thus strike a balance between rapid detectability of non-surgical motions and reduction in unnecessary stoppage of the surgical robotic system due to false positives.

FIG. 1 is a pictorial view of an example surgical robotic system 1 in an operating arena, in accordance with aspects of the subject technology. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or another person, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user displays 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. For example, the remote operator 9 at the user console 2 or the bedside operator 8 may use the handheld UIDs 14 to move the arm 4 from the stowed configuration to a preparation position above the patient 6 during the pre-operative setup. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table 5, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilisation and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table 5 to the right side of the patient, and a left arm 4 that is at the left side of the patient. An actuator 17 may include one or more motors that are controlled so that they drive the rotation of a joint of the arm 4 to, for example, change, relative to the patient, an orientation of an endoscope or a grasper of the surgical tool 7 that is attached to that arm.

In some aspects, the communication between the platform 5 and the user console 2 or the interface device may be through a control tower 3, which may translate user commands that are received from the user console 2 (and more particularly from the console computer system 16) or from the interface device into robotic control commands that are transmitted to the arms 4 on the robotic platform 5. The control tower 3 may also transmit status and feedback from the platform 5 back to the user console 2 or the interface device. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Prior to initiating surgery with the surgical robotic system 1, the surgical team can perform the preoperative setup. During the preoperative setup, the main components of the surgical robotic system (table 5 and robotic arms 4, control tower 3, and user console 2) are positioned in the operating room, connected, and powered on. The table 5 and robotic arms 4 may be in a fully-stowed configuration with the arms 4 under the table 5 for storage and/or transportation purposes. The surgical team can extend the arms from their stowed position for sterile draping. After draping, the arms 4 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 4 over the patient and attach each arm to its corresponding sleeve. The surgical robotic system 1 has the capability to uniquely identify each tool (endoscope and surgical instruments) as soon as it is attached and display the tool type and arm location on the open or immersive display 15 at the user console 2 and the touchscreen display on the control tower 3. The corresponding tool functions are enabled and can be activated using the master UIDs 14 and foot pedals 13. The patient-side assistant can attach and detach the tools, as required, throughout the procedure. The surgeon seated at the user console 2 can begin to perform surgery using the tools controlled by two master UIDs 14 and foot pedals 13. The system translates the surgeon's hand, wrist, and finger movements through the master UIDs 14 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 14 for instrument alignment and continue instrument control and motion. The foot pedals 13 may be used to activate various system modes, such as endoscope control and various instrument functions including monopolar and bipolar cautery, without involving surgeon's hands removed from the master UIDs 14.

The table 5 can be repositioned intraoperatively. For safety reason, all tool tips should be in view and under active control by the surgeon at the user console 2. Instruments that are not under active surgeon control must be removed, and the table feet must be locked. During table motion, the integrated robotic arms 4 may passively follow the table movements. Audio and visual cues can be used to guide the surgery team during table motion. Audio cues may include tones and voice prompts. Visual messaging on the displays at the user console 2 and control tower 3 can inform the surgical team of the table motion status.

Figure 2:
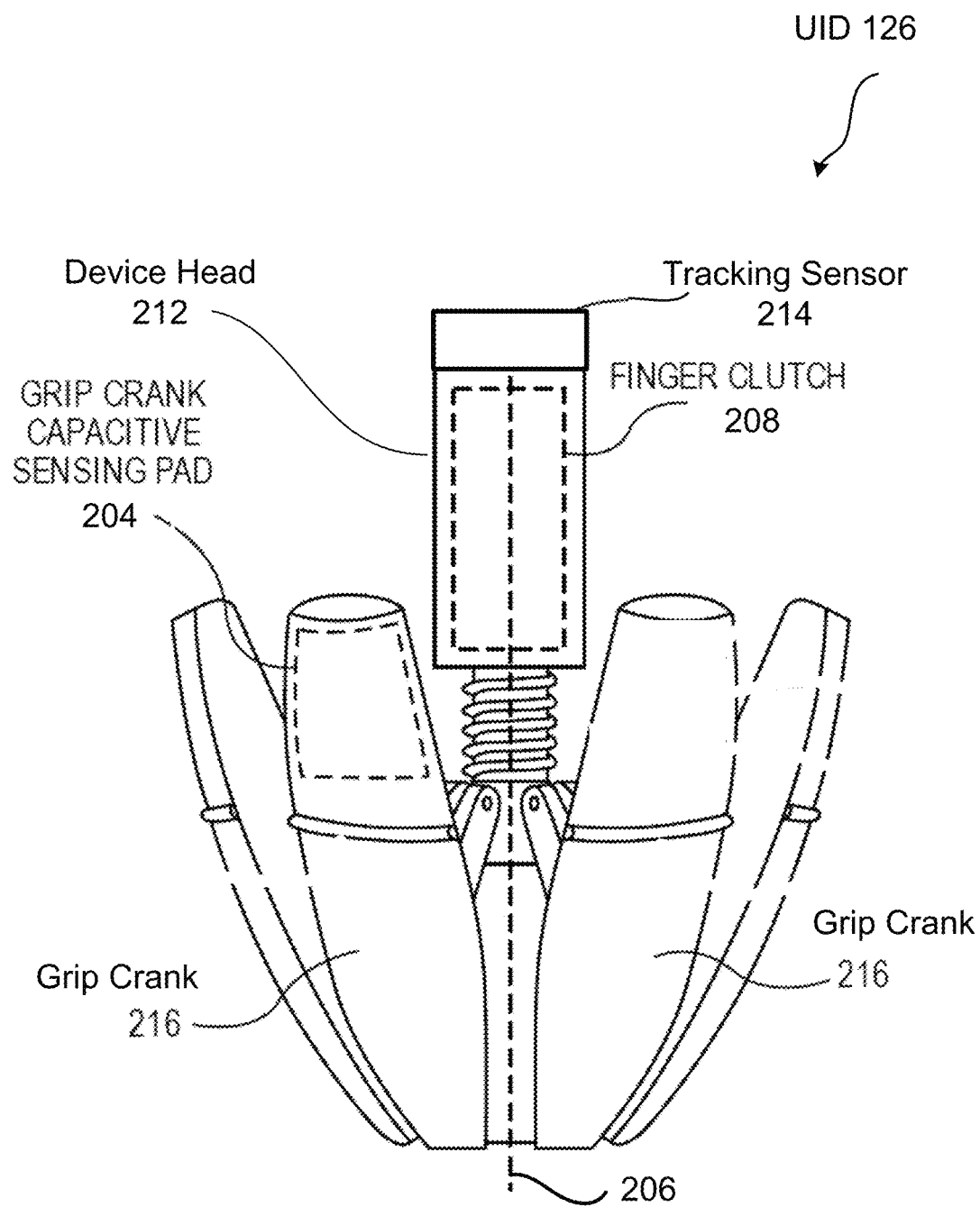
FIG. 2 is a side view of several touch sensitive surfaces of a UID, in accordance with aspects of the subject technology.

FIG. 2 is a side view of several touch sensitive surfaces of a UID, in accordance with aspects of the subject technology. UID 126 can include several touch sensitive surfaces. The touch sensitive surfaces can include capacitive and/or conductive elements that generate a signal in response to a touch by a user. Accordingly, by touching predetermined locations on UID 126, the user can command specific functions of surgical robotic system 1. The functions can be non-gripping functions. For example, the user may touch the capacitive sensing pads to command a camera view of an endoscope, a cursor on a display 15 of user console 2, etc.

In an embodiment, UID 126 includes a clutch mechanism to decouple movement of UID 126 from the control of the surgical robotic system 1. The clutch mechanism can be referred to as a finger clutch. The finger clutch may be so-termed because it may be actuated by a touch from a finger of the user. In an embodiment, a finger clutch 208 may be mounted on or integrated in a region of a device body as indicated by the dotted line. For example, device head 212 may include finger clutch 208. Finger clutch 208 may include a touch sensitive exterior surface of device head 212 that allows the user to pause teleoperation for an individual instrument that is being manipulated by UID 126. That is, when the user touches finger clutch 208, the touch may be detected as a clutch input. In response to the clutch input, control signals corresponding to movement of UID 126 detected by a tracking sensor may be discontinued. When the clutch input is removed (when the touch is ended) the movement of UID 126 may again cause a corresponding movement of the surgical robotic system 1. That is, when finger clutch 208 is unclutched, e.g., by removing a finger from finger clutch 208, UID movement may again be detected and input to the surgical robotic system 1 as a motion control input.

Finger clutch 208 of UID 126 may allow a user to reposition UID 126 within the workspace when a limit of the workspace has been reached. For example, by extending an arm fully from a start position in a direction while holding UID 126, the user may reach the limit of the workspace, e.g., an edge of the workspace. To reposition UID 126 within the workspace and allow for additional movement in the direction of the workspace edge, the user may touch the finger clutch 208 with an index finger to disconnect the surgical robotic system 1 from the movement of UID 126. The user may then move UID 126 back to the start position within the workspace and unclutch the surgical robotic system 1 by lifting the index finger from finger clutch 208. Additional movement in the first direction may then be performed by moving UID 126 to manipulate motion of surgical robotic system 1.

In one embodiment, finger clutch 208 may include a capacitive sensor that detects a change in the capacitance of the touch sensitive area of the device head 212 based on the proximity of the user's finger to, or when the user touches, the touch sensitive area of finger clutch 208. Finger clutch 208 may be located outside of a normal grasping area of UID 126. For example, finger clutch 208 may be distal to the exterior surfaces of grip cranks 216 that user holds during normal operation. Finger clutch 208 may, however, be within reach of a finger of the user when the user is manipulating UID 126. Accordingly, during normal operation, the user may extend the finger to touch finger clutch 208 and transmit a clutch signal to surgical robotic system 1.

Additional touch sensitive areas and capacitive sensors may be used to command different functions of UID 126. In an embodiment, UID 126 may include at least one grip crank capacitive sensing pad 204 mounted on grip crank 216. The exterior surface of grip crank 216 may include a touch sensitive area that covers an underlying grip crank capacitive sensing pad 204. In one embodiment, the construction of grip crank capacitive sensing pad 204 may be similar to the construction of the capacitive sensor of finger clutch 208. There may be multiple grip cranks, each with its grip crank capacitive sensing pad 204. The user may touch grip crank capacitive sensing pad 204 to push grip crank 216 toward the central axis 206 of UID 126 to command specific functions of surgical robotic system 1. UID 126 may determine how many fingers are holding UID 126 by measuring changes in the capacitance of grip crank capacitive sensing pad 204 for each grip crank 216.

In other embodiments, other types of proximity or contact sensors such as ones using optical sensing, thermal sensing, etc., may be placed at various locations on UID 126 to determine if UID 126 is being held or not. If UID 216 is being held, based on the locations of the sensors and the sensed signals, a processor within UID 216 may determine if the UID 216 is being held by fingers or is resting on the user's hand. If UID 216 is being held by fingers, such as when grip crank 216 are gripped, the tightness of the grip, the number of grip crank 216 gripped, or the number of fingers used may be determined. The processor may use information on which part of the hand is contacting UID 216, which part of UID 216 the user is contacting, the strength of the contact, etc., to determine if the user does not have full control of UID 216 for a threshold period of time. The threshold period of time may be a function of how and where the user is holding the UID.

UID 126 may include a tracking sensor 214 (e.g., a six-degree-of-freedom electromagnetic tracker) that generates a spatial state signal in response to movements of the UID. The spatial state signal may correspond to a position and/or orientation of UID 126 in free space. The spatial state signal may be used to control a spatial motion of an actuator of robotic arm 4 or the attached surgical tool to mimic the spatial motion of UID 126 in the hand of the user. Tracking sensor 214 may be an inertial sensor, such as an inertial measurement unit (IMU) that include an accelerometer, a gyroscope, a magnetometer, or one or more other transducers capable of converting physical movement into a corresponding electrical signal. For example, tracking sensor 214 may include a magnetic tracking probe capable of measuring six degrees of freedom, including physical displacement (e.g., translation in XYZ space or another suitable coordinate system), roll, pitch, and yaw of UID 126. Tracking sensor 214 may be used to detect a dropped UID 216 or other non-surgical motions of UID 216.

For example, after determining that the user does not have full control of UID 126 for a threshold period of time, tracking sensor 214 may detect if UID 126 is experiencing non-surgical motions. In one embodiment, tracking sensor 214 may detect velocity, acceleration, and jerk along the three-dimensional XYZ space to recognize non-surgical motions such as bobbling, throwing, swinging, freefalling, etc., of UID 126. For example, an acceleration magnitude of 0 in the vertical direction may indicate a freefall drop. A high jerk may indicate bobbling or throwing. A high acceleration may indicate throwing or swinging. A high rotational acceleration or velocity may indicate slipping, rolling or throwing of UID 126. By conditioning analysis of the sensed data from tracking sensor 126 on the threshold determination that the UID is not being held based on the sensed signals from the proximity or contact sensors, the robustness of the detection of non-surgical motions is increased and the probability of false positives is reduced.

Figure 3:
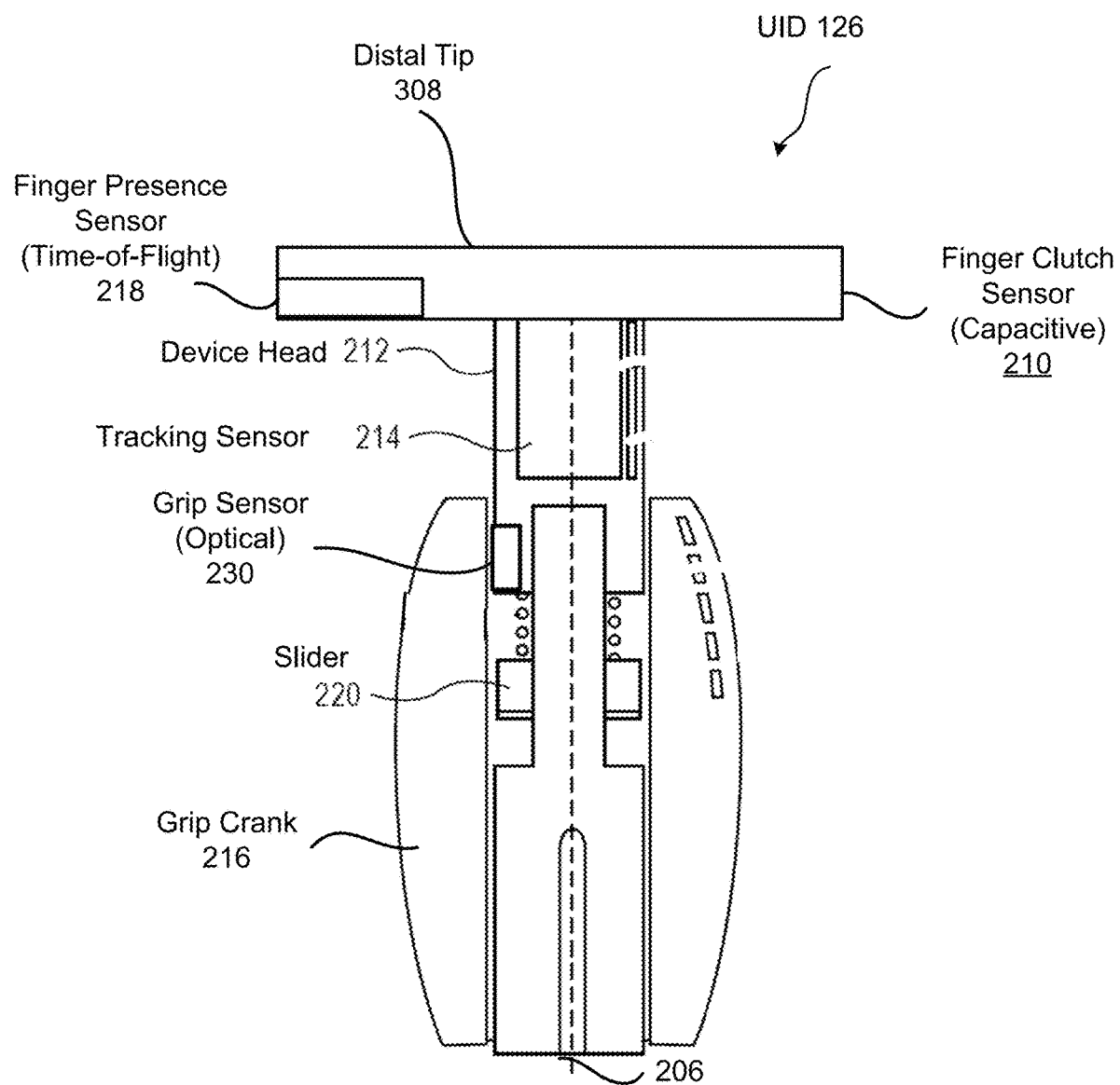
FIG. 3 shows a sectional view of a UID that has a capacitive finger clutch sensor, an optical finger presence sensor, an optical grasp open/close sensor, and an inertial motion sensor, with the UID in a closed configuration, in accordance with aspects of the subject technology.

FIG. 3 shows a sectional view of another UID 126 that has a capacitive finger clutch sensor 210, an optical finger presence sensor 218, an optical grasp open/close sensor 230, and a tracking sensor 214, with the UID in a closed configuration, in accordance with aspects of the subject technology. Capacitive finger clutch sensor 210, optical finger presence sensor 218, and optical grip sensor 230 are proximity or contact sensors whose sensed signals may be used to determine whether, where, and how UID 126 is being held to determine if a user has full control of UID 126.

For example, one or more optical finger presence sensors 218 may be positioned on a distal tip of UID 126 to emit radiant energy toward a proximal end of UID 126. When a user holds UID 126, such as by griping grip crank 216, optical finger presence sensors 218 may detect the radiant energy reflected from one or more of the user's fingers. By measuring the strength and the time-of-flight of the reflected signals, optical finger presence sensors 218 or a processor of UID 126 may determine how many fingers are holding UID 126 and which surface of UID 126 or which grip crank 216 the fingers are touching.

An optical grip sensor 230 may be positioned on device head 212 of UID 126 to measure the strength of the user's grip by measuring the position or displacement of a slider 220. When the user applies pressure to push grip crank 216 toward the central axis 206 of UID 126, slider 220 may be displaced along the central axis 206 toward device head 212. The displacement of slider 220 may cause a low spring force to be exerted against the user's pressure. The amount of displacement of slider 220 may correspond to the strength of the pressure applied on grip crank 216, and may be measured by the distance between grip crank 216 and central axis 206. For example, FIG. 3 shows the grip crank 216 in the closed configuration, when the user tightly grips UID 126 and slider 220 is displaced closest to device head 212. Optical grip sensor 230 may emit radiant energy toward slider 220 and may measure the radiant energy reflected from slider 220. By measuring the time-of-flight of the reflected signals, optical grip sensor 230 or a processor of UID 126 may determine the strength of the user's grip. In one embodiment, by analyzing how the UID 126 is held, which fingers are holding UID 126 as determined from optical finger presence sensors 218, and the strength of the grip as determine from optical grip sensor 230, UID 126 may determine if the user has full control of UID 126.

After determining that the user does not have full control of UID 126 for a threshold period of time, tracking sensor 214 may detect high velocity, acceleration, and jerk along the three-dimensional XYZ space to recognize non-surgical motions such as bobbling, throwing, swinging, freefalling, etc., of UID 126. For example, if optical finger presence sensors 218 and optical grip sensor 230 indicate that the user is no longer in contact with UID 126, and tracking sensor 214 detects an acceleration magnitude of 0 in the vertical direction for a threshold period of time, UID 126 may determine that it has been dropped. In another example, if optical finger presence sensors 218 and optical grip sensor 230 indicate that the user is not holding UID 126 with two non-adjacent fingers, the UID is laying on the user's open palm, or there is a high velocity release of grip crank 216, and tracking sensor 214 detects high rotational acceleration or velocity, UID 126 may determine that it has rolled out of the user's hand. UID 126 may automatically engage the finger clutch to decouple a robotic arm from the non-surgical motions of UID 126.

A capacitive finger clutch sensor 210 may be positioned on distal tip 308 of UID 126 to detect the user's finger for decoupling a robotic arm from the movement of UID 126. As in FIG. 2, capacitive finger clutch sensor 210 may detect a change in the capacitance based on the proximity of the user's finger to, or the contact of the user's finger with, capacitive finger clutch sensor 210. In one embodiment, to provide a safeguard against the user not touching capacitive finger clutch sensor 210 with sufficient force when repositioning UID 126 within the workspace, UID 126 may determine if there is an anomaly in the user's control of the finger clutch. For example, capacitive finger clutch sensor 210 may detect that the user's finger is not fully touching capacitive finger clutch sensor 210 for a threshold period of time even though the user is holding UID 126 as indicated by optical finger presence sensors 218 and optical grip sensor 230. Based on this determination, UID 126 may determine if it is experiencing non-surgical motions using the tracking sensor 214. If tracking sensor 214 detect that UID 126 is experiencing velocity, acceleration, or jerk that exceeds a maximum threshold or that lasts longer than a threshold period of time, UID 126 may indicate non-surgical motions.

UID 126 may include other types of proximity, contact, or tracking sensors. For example, instead of capacitive or optical sensors, thermal or infrared sensors that detect thermal energy emanating from a user's hand, ultrasonic sensors that detect reflected ultrasound signal, etc., may be used to determine if the user has full control of UID 126. In one embodiment, a positional sensor that detects high velocity or acceleration toward the ground or away from the surgery workspace may indicate a drop or other non-surgical motions. In one embodiment, temporal information may be used to detect the phases of non-surgical motions. For example, UID 126 may apply different time thresholds or detection criteria to detect that UID 126 is in a slipping motion, rolling out of a user's hand, or is in freefall.

Figure 4:
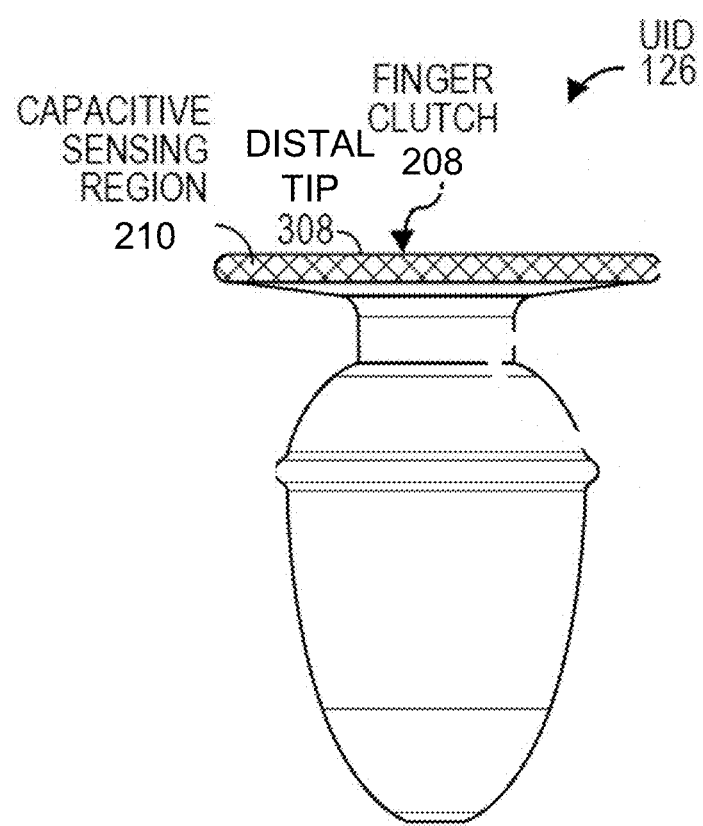
FIG. 4 is a side view of another UID with a capacitive finger clutch sensor, in accordance with aspects of the subject technology.

FIG. 4 is a side view of another UID 126 with a capacitive finger clutch sensor, in accordance with aspects of the subject technology. Capacitive sensing region 210 of finger clutch 208 may be positioned at a disc portion of a distal tip 308. Capacitive sensors for sensing the touch of the user's hand may be positioned around the cylindrical body of UID 216. In one embodiment, one or more optical finger presence sensors may be positioned at distal tip 308 to have an obstructed view of each contact surface of interest. As in FIGS. 2 and 3, sensed signals from the proximity, contact, and tracking sensors may be combined to increase the robustness of the detection of non-surgical motions and to reduce the probability of false positives.

Figure 5:
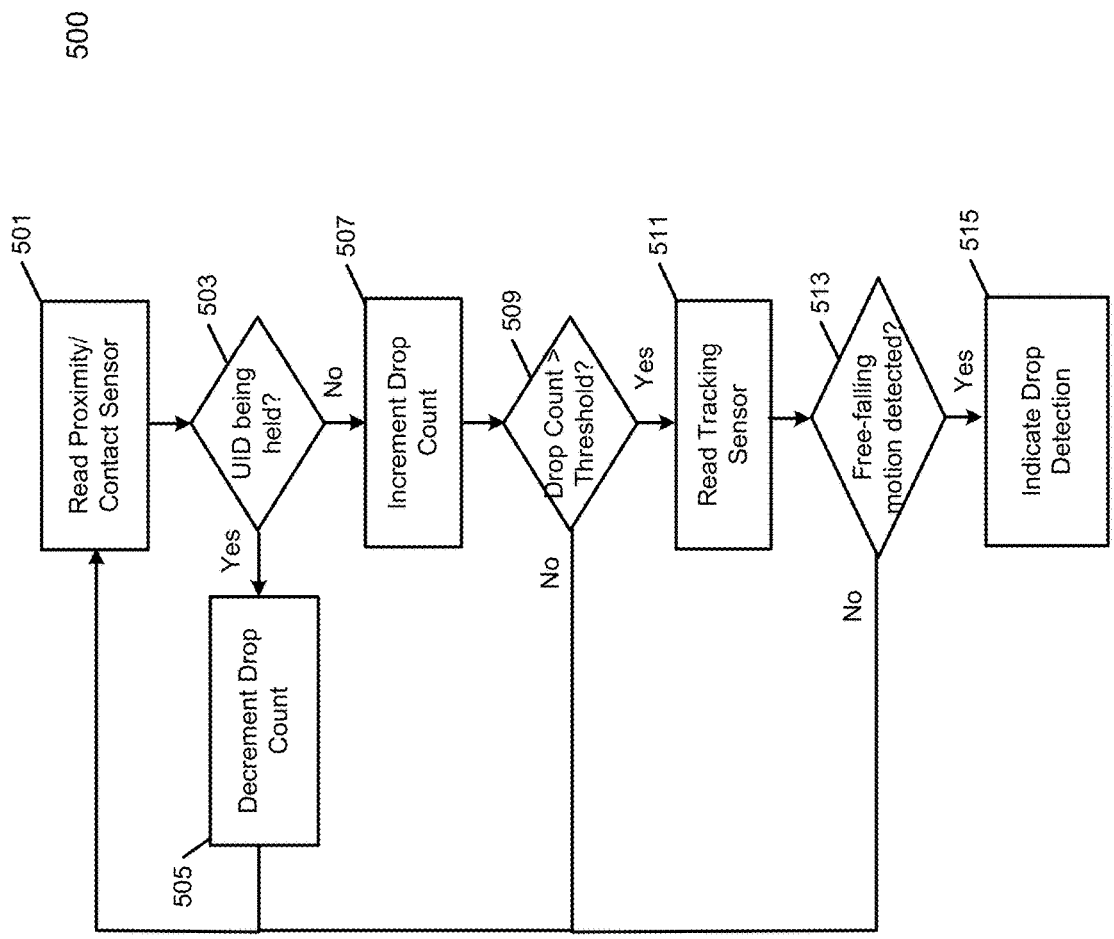
FIG. 5 is a flow chart illustrating a method of detecting a drop of the UID using a combination of proximity or contact sensors and motion tracking sensors, in accordance with aspects of the subject technology.

FIG. 5 is a flow chart illustrating a method 500 of detecting a drop of an UID using a combination of proximity or contact sensors and motion tracking sensors, in accordance with aspects of the subject technology. The UID may be the UID 14 or UID 126 of FIG. 1, 2, 3, or 4. Method 500 may be implemented by software, hardware, or a combination of software and hardware running on the UID, console computer system 16, or other parts of surgical robotic system 1.

In operation 501, method 500 reads sensed data from one or more proximity or contact sensors. Proximity or sensors contacts may use capacitive, optical, thermal, or other types of sensing mechanism, and may be placed at various locations on the UID to determine if surface areas of interest on the UID are touched by or in close proximity to a user's hand. For example, capacitive sensing pads on grip cranks may sense the grip of the user's fingers based on the change in the capacitance of touch sensitive areas of the capacitive sensing pads. In one embodiment, an optical finger presence sensor with an unobstructed view of the grip cranks may sense the strength and time-of-flight of reflected radiant energy to determine the position of the user's fingers on the grip cranks. In one embodiment, an optical grip sensor may detect the time-of-flight of signals reflected from the displaced position of a slider of the crank linkage due to the user gripping the grip cranks to determine the strength of the user's grip.

In operation 503, method 500 determines if the UID is being held or that the user has full control of the UID based on the sensed data from the proximity or contact sensors. For example, based on what surfaces of the UID has user contact and the strength of the user contact, method 500 may determine how the UID is being held, such as whether the UID is held by fingers or the palm of the user's hand, the orientation of the hand holding the UID, the tightness of the grip, etc. If the proximity or contact sensors indicate that the UID is not in contact with any part of the user's hand, method 500 may determine that the UID is not being held. In one embodiment, method 500 may determine that the user does not have full control of the UID even if the UID is in contact with the user's hand, such as when the proximity or contact sensors indicate that the UID is being held with two adjacent fingers without any support from the user's palm.

In operation 507, if it is determined that the UID is not being held or that the user does not have full control of the UID, method 500 increments a drop count. The drop count keeps track of the length of time that the UID is either not being held entirely or not being held with sufficient user control, either continuously or intermittently. Otherwise, if it is determined that the user has full control of the UID, method 500 decrements the drop count at operation 505, and method 500 returns to operation 501 to re-read sensed data from the proximity or contact sensors. The drop count may be initialized to zero at the start of method 500 and may not be decremented below zero.

In operation 509, method 500 compares the drop count against a threshold to determine if the UID has not been held entirely or has not being held with sufficient user control for a threshold length of time. The threshold may be a function of whether, how, and where the user is holding the UID. For example, if the UID is not being held at all, the threshold may be shorter than the periodic interval with which commands are issued to a robotic arm so that the robotic arm may be decoupled from the motion of the UID at the next command instance. On the other hand, if the UID is being held but with insufficient user control, the threshold may be longer to allow time for the user to regain full control of the UID without prematurely decoupling the robotic arm.

In operation 511, if the drop count is greater than the threshold, method 500 reads sensed data from the track sensor to detect the motion of the UID. The track sensor may measure six degrees of freedom, including physical displacement (e.g., translation in XYZ space or another suitable coordinate system), roll, pitch, and yaw of the UID. The tracking sensor may also detect velocity, acceleration, and jerk along the three-dimensional XYZ space to recognize non-surgical motions such as bobbling, throwing, swinging, freefalling, etc., of the UID. Otherwise, if the drop count is not greater than the threshold, method 500 returns to operation 501 to re-read sensed data from the proximity or contact sensors to determine if the UID is still not being held or not being held with sufficient user control.

In operation 513, method 500 determines from the sensed data of the tracking sensor if free-falling motion is detected. For example, an acceleration magnitude of 0 in the vertical direction may indicate a freefall drop. In one embodiment, operation 513 may detect other non-surgical motions. In one embodiment, operation 513 may determine if the detected velocity, acceleration, and jerk exceeds a maximum threshold. The maximum threshold may be a function of the phases of a fall or other non-surgical motion.

In operation 515, if a free-falling motion is detected, method 500 indicates a drop detection. Method 500 may issue a command or automatically engage the finger clutch to decouple a robotic arm from the motion of the UID. Otherwise, if a free-falling motion is not detected, method 500 returns to operation 501 to re-read sensed data from the proximity or contact sensors. In one embodiment, operation 515 may indicate other non-surgical motions. By conditioning the analysis of the sensed data from the tracking sensor on the threshold determination that the UID is not being held based on the proximity or contact sensors, method 500 increases the robustness of the detection of non-surgical motions and reduces the probability of false positives.

Figure 6:
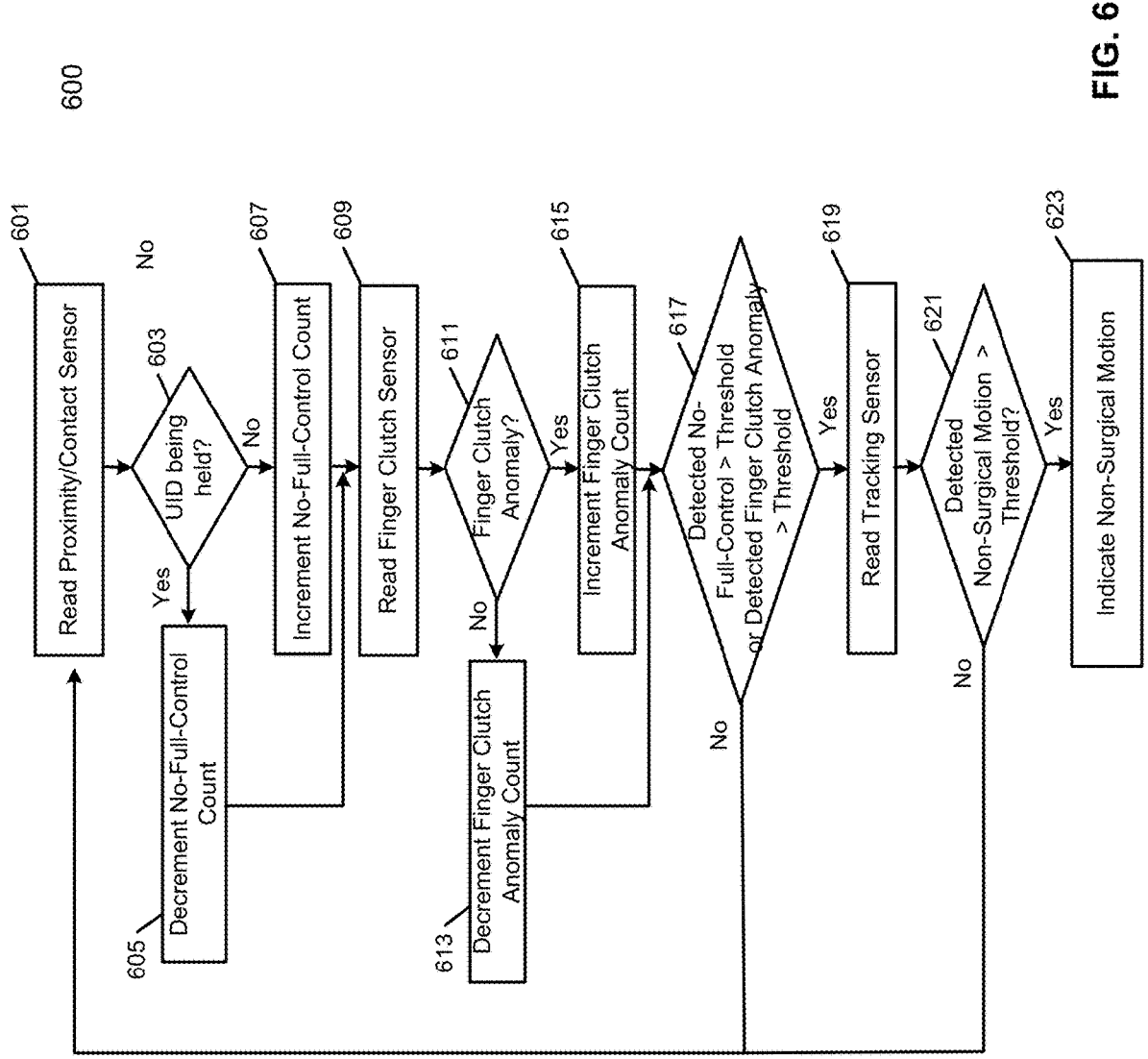
FIG. 6 is a flow chart illustrating a method of detecting a non-surgical motion of the UID using a combination of proximity or contact sensors, finger clutch sensors, and motion tracking sensors, in accordance with aspects of the subject technology.

FIG. 6 is a flow chart illustrating a method 600 of detecting a non-surgical motion of the UID using a combination of proximity or contact sensors, finger clutch sensors, and motion tracking sensors, in accordance with aspects of the subject technology. The UID may be the UID 14 or UID 126 of FIG. 1, 2, 3, or 4. Method 500 may be implemented by software, hardware, or a combination of software and hardware running on the UID, console computer system 16, or other parts of surgical robotic system 1.

In operation 601, method 600 reads sensed data from one or more proximity or contact sensors to determine if surface areas of interest on the UID are touched by or in close proximity to a user's hand. In operation 603, method 600 determines if the UID is being held or that the user has full control of the UID based on the sensed data from the proximity or contact sensors. In operation 607, if it is determined that the UID is not being held or that the user does not have full control of the UID, method 600 increments a no-full-control count. The no-full-control count may be initialized to zero at the start of method 600 and may not be decremented below zero. Operations 601, 603, and 607 are similar to operations 501, 503, and 507 of FIG. 5 and the details of these operations are not repeated for brevity. Otherwise, if it is determined that the user has full control of the UID, method 600 decrements the no-full-control count at operation 605. After either incrementing or decrementing the no-full-control count, method 600 proceeds to operation 609 to sense data from the finger clutch.

In operation 609, method 600 detects sensed data from the finger clutch that may be actuated by the user to decouple movement of the UID from the motion of a robotic arm to pause teleoperation for an individual instrument that is being manipulated by UID. A capacitive sensor of the finger clutch may detect a change in the capacitance of a touch sensitive area of the finger clutch based on the proximity of the user's finger to, or the contact of the user's finger with, the touch sensitive area.

In operation 611, method 600 determines if there is an anomaly in the user's control of the finger clutch based on the sensed data from the finger clutch. For example, the capacitive finger clutch sensor may detect that the user's finger is not fully touching the touch sensitive area of the finger clutch or is not touching the touch sensitive area with sufficient force to fully engage the finger clutch. Detecting an anomaly in the user's control of the finger clutch safeguards against the user falsely assuming that the finger clutch is engaged to decouple the robotic arm when it is not during operations such as when repositioning the UID within the workspace.

In operation 615, if it is determined that there is an anomaly in the user's control of the finger clutch, method 600 increments a finger clutch anomaly count. The finger clutch anomaly count keeps track of the length of time that the user's control of the finger clutch is considered anomalous, either continuously or intermittently. Otherwise, if it is determined that the user is controlling the finger clutch normally, method 613 decrements the finger clutch anomaly count at operation 613. The finger clutch anomaly count may be initialized to zero at the start of method 600 and may not be decremented below zero. After either incrementing or decrementing the finger clutch anomaly count, method 600 proceeds to operation 617 to determine whether the user has full control of the UID.

In operation 617, method 600 compares the no-full-control count against a no-full-control threshold and compares the finger clutch anomaly count against a finger clutch anomaly threshold. The no-full-control threshold may be a function of whether, how, and where the user is holding the UID. Similarly, the finger clutch anomaly threshold may be a function of whether and how the user is controlling the finger clutch. If the no-full-control count is greater than the no-full-control threshold or the finger clutch anomaly count is greater than the finger clutch anomaly threshold, the user is considered not to have full control of the UID or not to operate the finger clutch normally. Method 600 then proceeds to operation 619 to read sensed data from the tracking sensor. Otherwise, if the no-full-control count is not greater than the no-full-control threshold and the finger clutch anomaly count is not greater than the finger clutch anomaly threshold, method 600 returns to operation 601 to re-read sensed data from the proximity or contact sensors to determine if the user has full control of the UID.

In operation 619, method 600 reads sensed data from the track sensor to detect the motion of the UID. As in operation 511, the track sensor may measure six degrees of freedom, including physical displacement, roll, pitch, and yaw of the UID, and velocity, acceleration, and jerk along the three-dimensional XYZ space.

In operation 621, method 600 analyzes the sensed data of the tracking sensor to determine if the UID is experiencing non-surgical motions such as bobbling, throwing, swinging, freefalling. For example, an acceleration magnitude of 0 in the vertical direction may indicate a freefall drop. A high jerk may indicate bobbling or throwing. A high acceleration may indicate throwing or swinging. A high rotational acceleration or velocity may indicate slipping, rolling or throwing of the UID. In one embodiment, the velocity, acceleration, or jerk may be compared against a threshold to determine if there are non-surgical motions. In one embodiment, the duration of the non-surgical motion may be compared against a time threshold. The time threshold may be a function of the phases of the non-surgical motion detected. For example, different time thresholds or detection criteria may be used to detect that the UID is experiencing a slipping motion, is rolling out of a user's hand, or is in freefall.

In operation 623, if a non-surgical motion is detected, method 600 indicates a non-surgical motion detection. Method 600 may issue a command or automatically engage the finger clutch to decouple a robotic arm from the motion of the UID. Otherwise, if a non-surgical motion is not detected, method 600 returns to operation 601 to re-read sensed data from the proximity or contact sensors. By conditioning the analysis of the sensed data from the tracking sensor on the threshold determination that the user does not have full control of the UID or does not operate the finger clutch normally based on the proximity or contact sensors, method 600 increases the robustness of the detection of non-surgical motions and reduces the probability of false positives.

Figure 7:
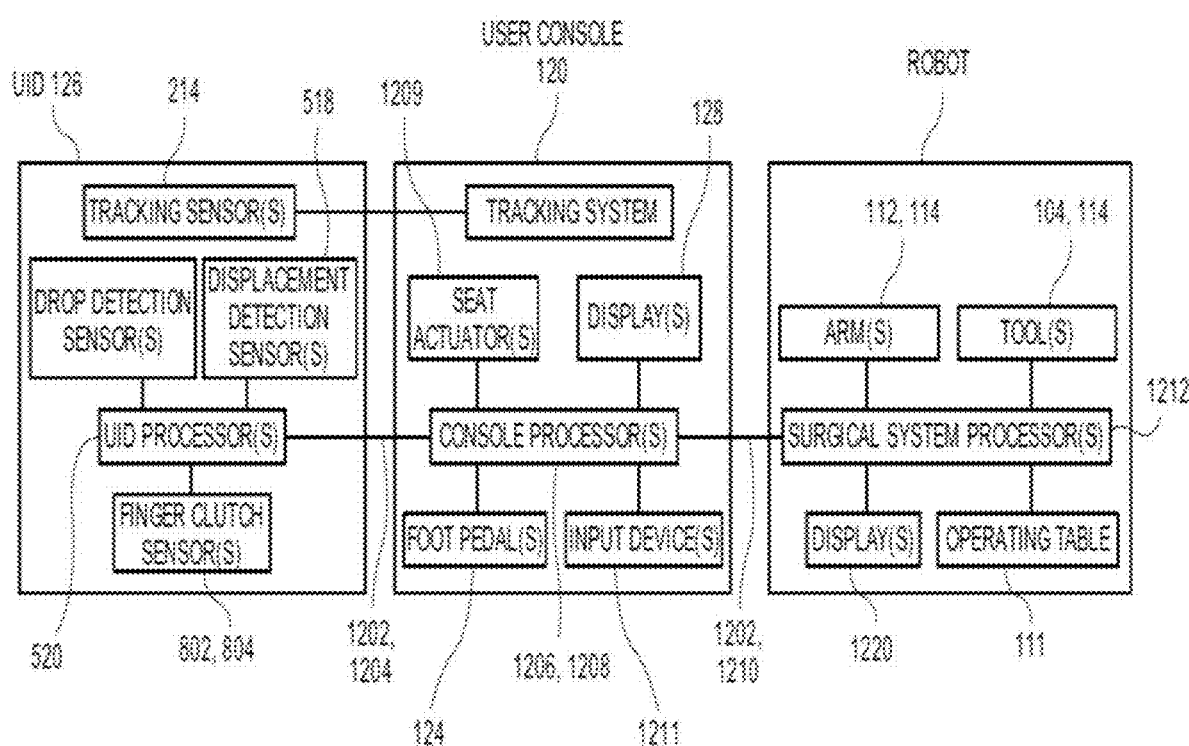
FIG. 7 is a block diagram illustrating exemplary hardware components of a surgical robotic system, in accordance with aspects of the subject technology.

FIG. 7 is a block diagram illustrating exemplary hardware components of a surgical robotic system, in accordance with aspects of the subject technology. The surgical robotic system can include user console 120 having computer system 110 and one or more UIDs 126. Computer system 110 and UID 126 have circuitry suited to specific functionality, and thus, the diagrammed circuitry is provided by way of example and not limitation.

User console 120 can control portions of surgical robotic system 100, e.g., robotic arms 112 and/or surgical tools 104. UID 126 may be communicatively coupled to computer system 110 and/or surgical robotic system 100 to provide input commands to control surgical robotic system 100. For example, UID 126 may communicate electrical control signals 1202 to computer system 110, e.g., spatial state signals generated by UID processor 520 in response to signals from tracking sensor 214, grip signals generated by UID processor 520 in response to signals from grip sensor 518, clutch signals generated by UID processor 520 in response to detected changes in capacitance of finger clutch sensor 802, and other signals generated by UID processor 520 in response to sensed signals from other proximity or contact sensors. UID processor 520 may process the sensed signals from the proximity, contact, and tracking sensors to determine if UID 126 is being dropped or is experiencing other non-surgical motions as described. UID processor 520 may generate input command signals to cause motion of surgical robotic system 100, or to pause motion of surgical robotic system 100.

The input commands signals may be transmitted by UID processor 520 to a console processor 1206 of computer system 110 via a wired or wireless connection. For example, UID 126 may transmit the control signals 1202 to console processor 1206 via electrical wire 1204. Alternatively, UID 126 may transmit control signals 1202 to console processor 1206 via a wireless communication link. The wireless communication link may be established by respective RF circuitry of computer system 110 and UID 126. The wireless communication can be via radiofrequency signals, e.g., Wi-Fi or short range signals and/or suitable wireless communication protocols such as Bluetooth.

Console processor 1206 of computer system 110 may execute instructions to carry out the different functions and capabilities described above. Instructions executed by console processor(s) 1206 of user console 120 may be retrieved from a local memory 1208, which may include a non-transitory machine-readable medium. The instructions may be in the form of an operating system program having device drivers to control components of surgical robotic system 100, e.g., actuators 114 operatively coupled to robotic arm(s) 112 or surgical tool(s) 104.

In an embodiment, console processor 1206 controls components of user console 120.

For example, one or more seat actuators 1209 can receive commands from console processor 1206 to control movement of seat 10. Seat actuator(s) 1209 can move seat 10 in one or more degrees of freedom, such as forward/backward, backrest tilt, headrest position, etc. Console processor 1206 can also transmit video data for presentation on display 128. Accordingly, console processor 1206 can control operation of user console 120. Input commands to seat actuator(s) 1209 or console processor 1206 can be entered by the user via foot pedal(s) 13 or another interface device 1211 such as a keyboard or a joystick.

Console processor 1206 can output control signals 1202 to surgical robotic system 100 via a link 1210. Control signals 1202 may be transmitted to control movement of surgical robotic system 100. Computer system 110 may be communicatively coupled to surgical robotic system 100 via wired or wireless links to output control signals 1202 to one or more surgical robotic system processor(s) 1212. For example, at least one processor 1212 can be located in control tower 130, and may be communicatively coupled to system components, such as surgical robotic platform 111 or one or more displays 1220. Actuators 114 of surgical robotic system 100 may receive control commands from surgical system processor 1212 to cause motion corresponding to movement of UID 126 or to pause motion of surgical robotic system 100 by clutching and/or disconnecting an interlock of surgical robotic system 100 when the user touches the finger clutch or drops UID 126.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. A method for controlling a surgical robotic system, comprising:
    sensing, by a user interface device (UID), contact data from one or more contact sensors, the contact data indicating contact by a user of parts of the UID;
    determining the UID is not being held by the user for a length of time greater than a time threshold based on the contact data from the contact sensors;
    responsive to determining that the length of time the UID is not being held is greater than the time threshold, sensing, from one or more tracking sensors of the UID, motion data indicating a motion of the UID;
    determining a free-falling motion of the UID based on the motion data; and
    decoupling the surgical robotic system from a movement of the UID in response to the free-falling motion of the UID.

2. The method of claim 1, wherein sensing, by the UID, contact data from the one or more contact sensors comprises:
    sensing through a sensing mechanism that comprises capacitive, optical, or thermal that parts of the UID are touched or are in close proximity with the user's hand.

3. The method of claim 1, wherein sensing, by the UID, contact data from the one or more contact sensors comprises:
    sensing through a sensing mechanism that comprises capacitive, optical, or thermal, a strength of the contact by the user's hand with parts of the UID.

4. The method of claim 1, wherein determining the UID is not being held by the user for a length of time greater than a time threshold based on the contact data from the contact sensors comprises:
    determining that for the length of time greater than the time threshold the UID has no contact with any part of the user's hand or the UID is not being held firmly by the user's hand to prevent the UID from falling.

5. The method of claim 1, wherein determining the UID is not being held by the user for a length of time greater than a time threshold based on the contact data from the contact sensors comprises:
    determining how the UID is being held by the user's hand, and wherein the time threshold is a function of determining how the UID is being held by the user's hand.

6. The method of claim 1, wherein the motion data from the one or more tracking sensors comprises:
    a physical displacement of the UID in three dimensions;
    an orientation of the UID in roll, pitch, and yaw; or
    a measure of velocity, acceleration, and jerk along the three dimensions.

7. The method of claim 1, further comprising:
    determining a non-surgical motion of the UID based on the motion data, wherein the non-surgical motion of the UID comprises a bobbling, throwing, swinging, slipping, or rolling motion of the UID; and
    decoupling the surgical robotic system from a movement of the UID in response to the non-surgical motion of the UID.

8. The method of claim 1, further comprising:
    determining that the UID is being held firmly by the user's hand to prevent the UID from falling based on the contact data from the contact sensors or determining a surgical motion of the UID based on the motion data; and
    allowing the UID to control the surgical robotic system in response to motions of the UID.

9. The method of claim 1, wherein sensing, by a user interface device (UID), contact data from one or more contact sensors comprises:
    sensing contact data from a sensor for a finger clutch of the UID, wherein when the sensor for the finger clutch detects the user's touch on the finger clutch the surgical robotic system is decoupled from a movement of the UID.

10. The method of claim 9, further comprising:
    determining that there is an anomaly in control of the finger clutch by the user based on the contact data from the sensor for the finger clutch;

determining whether a length of time of the anomaly in the user's control of the finger clutch is greater than a second time threshold; and sensing, by the UID, motion data from the one or more tracking sensors in response to determining that the length of time of the anomaly in the user's control of the finger clutch is greater than the second time threshold to decouple the surgical robotic system from a movement of the UID.

11. The method of claim 10, wherein determining that there is an anomaly in the control of the finger clutch by the user comprises:

determining that the finger clutch is not touched by the user's hand with a sufficient force to fully engage the finger clutch to decouple the surgical robotic system from a movement of the UID.

12. A user interface device (UID) for a surgical robotic system, comprising:

one or more contact sensors configured to generate contact data that indicates contact by a user of parts of the UID;

one or more tracking sensors configured to generate motion data that indicates motions of the UID;

a processor configured to:
 determine that the UID is not being held by the user for a duration greater than a time threshold based on the contact data:
 responsive to determining that the UID is not being held by the user for the duration greater than the time threshold, sense, from the one or more tracking sensors the motion data;
 determine a free-falling motion of the UID based on the motion data; and
 decouple the surgical robotic system from a movement of the UID in response to the determination that the UID is not being held by the user for the duration greater than the time threshold and the determination of the free-falling motion of the UID.

13. The UID of claim 12, wherein the one or more contact sensors comprises one or more capacitive, optical, or thermal sensors, wherein the contact data comprises:

data that indicates that parts of the UID are touched by the user's hand;

data that indicates that parts of the UID are in close proximity with the user's hand; or data that indicates a strength of the contact by the user's hand.

14. The UID of claim 12, wherein the processor configured to determine that the UID is not being held by the user for a duration greater than a time threshold comprises the processor is configured to:

determine that the has no contact with any part of the user's hand or the UID is not being held firmly by the user's hand to prevent the UID from falling.

15. The UID of claim 12, wherein the motion data from the one or more tracking sensors comprises:

a physical displacement of the UID in three dimensions;
an orientation of the UID in roll, pitch, and yaw; or
a measure of velocity, acceleration, and jerk along the three dimensions.

16. The UID of claim 12, wherein the processor is further configured to perform operations comprising:

determine a non-surgical motion of the UID based on the motion data, wherein the non-surgical motion of the UID comprises a bobbling, throwing, swinging, slipping, or rolling motion of the UID; and decouple the surgical robotic system from a movement of the UID in response to the determination of the non-surgical motion of the UID.

17. The UID of claim 12, wherein the one or more contact sensors comprise a sensor for a finger clutch of the UID, and wherein the sensor for the finger clutch generates contact data that detects the user's touch of the finger clutch decouple the surgical robotic system from a movement of the UID.

18. The UID of claim 17, wherein the processor is further configured to perform operations comprising:

determine that there is an anomaly in control of the finger clutch by the user for a duration longer than a second time threshold based on the contact data from the sensor for the finger clutch;

determine a non-surgical motion of the UID based on the motion data; and decouple the surgical robotic system from a movement of the UID in response to the determination that the duration of the anomaly in the user's control of the finger clutch is greater than the second time threshold and the determination of the non-surgical motion of the UID.

19. A surgical robotic system, comprising:
an operating table;
a plurality of robotic arms coupled to the operating table;
a user interface device (UID) configured to:
 receive contact data from one or more contact sensors configured to sense contact by a user of part of the UID;
 determine whether the UID is held based on the contact data;
 responsive to determining that the UID is not held
  receive motion data from one or more tracking sensors configured to measure motions of the UID, and
  determine whether the UID is in a free-fall motion based on the motion data; and
 responsive to determining that the UID is held, generate an input command to one of the robotic arms based on the motions of the UID; and
a computer communicatively coupled to the UID and the plurality of robotic arms, wherein the computer is configured to:
 receive the input command from the UID; and
 generate a control command to manipulate one of the robotic arms in response to the input command.

20. The surgical robotic system of claim 19, wherein the UID is further configured to generate a stop command to decouple one of the robotic arms from being manipulated in response to the input command generated by the UID when the UID is determined not to be held for a duration greater than a time threshold and the motion data indicates that the UID is in the free-falling motion.

* * * * *